United States Patent [19]

Solomonow et al.

[11] Patent Number: 5,643,329

[45] Date of Patent: Jul. 1, 1997

[54] SYSTEM FOR MAINTAINING A DESIRED SPINAL CURVATURE OF A USER SUFFERING FROM IMPROPER ALIGNMENT OF THE VERTEBRAE OF THE SPINE

[76] Inventors: Moshe Solomonow, 4916 Green Acres Ct., Metairie, La. 70003; Robert D'Ambrosia, 2 Lakewood Estates Dr., New Orleans, La. 70131

[21] Appl. No.: 545,958

[22] Filed: Oct. 20, 1995

[51] Int. Cl.$^6$ .................................................. A61N 1/18
[52] U.S. Cl. ............................. 607/43; 128/781; 607/115
[58] Field of Search ............................ 607/43, 46, 48; 128/774, 781, 874, 905

[56] References Cited

U.S. PATENT DOCUMENTS 4,781,180  11/1988  Solomonow ............................ 128/80

OTHER PUBLICATIONS

Andersson, *Seminars in Spine Surgery*, 5,1:3–9, 1993.
Cooper et al., *Annals of Rheumatic Diseases*, 52:413–415, 1993.
Cooper et al., *Spine* 18,5:610–616, 1993.
Cassisi et al., *Spine* 18, 2:245–251, 1993.
Parkkola et al., *Spine* 18,7:830–836, 1993.
Hides et al., *Spine* 19,2:165–172, 1994.
Styf, *Spine* 12,7:675–679, 1987.
Konno et al., *Spine* 19,19:2186–2189, 1994.
Grabiner et al., *Spine*, 17,10:1219–1223, 1992.
Sihvonen et al., *Spine*, 18,5:575–581, 1993.
Lahad et al., *JAMA* 272,16:1286–1291, 1994.
Hansen et al., *Spine*, 18,1:98–107, 1993.
Risch et al., *Spine* 18,2:232–238, 1993.
Frost et al., *British Med Journal*, 310:151–154, 1995.
Lieber, *Develop Med and Child Neurology* 28:662–670, 1986.
Solomonow et al., *Am J Physical Medicine*, 62,2:71–82, 1983.
Solomonow et al., *Am J Physical Medicine*, 62,3:117–122, 1983.
Solomonow et al., *Orthopedics*, 12,10:1309–1315, 1989.
Solomonow, In book: *Neural Prostheses*, R. Stein et al. (editors), Oxford Press, Chap. 10:202–232, 1992.
Hirokawa et al., *Arch Phys Med Rehabil*, 71:687–694, 1990.

*Primary Examiner*—Jeffrey R. Jastrzab

[57] ABSTRACT

A system for maintaining a desired spinal curvature of a user suffering from improper alignment of the vertebrae of the spine. In it's broad aspects, it comprises a sensor feedback system and electrodes. The sensor feedback system measures spinal curvature, determines whether selected conditions have been met warranting the application of electrical stimulation and provides information regarding the determination to an electronic stimulator. The electrodes are spaceably mounted on selected portions of the user's back. They are in electrical communication with the electronic stimulator for causing contraction of the back muscles at selected levels, thus providing alignment of the spinal vertebrae. The sensor feedback system includes a sensor assembly which comprises an upper elongated rigid segment, a lower elongated rigid segment and a sensor. The upper elongated rigid segment is positionable adjacent the user's upper spine. The lower elongated rigid segment is positionable adjacent the posterior pelvic region. The sensor is mounted on a flexible middle segment between the upper segment and the lower segment. The sensor is so positioned as to measure lordosis.

18 Claims, 3 Drawing Sheets

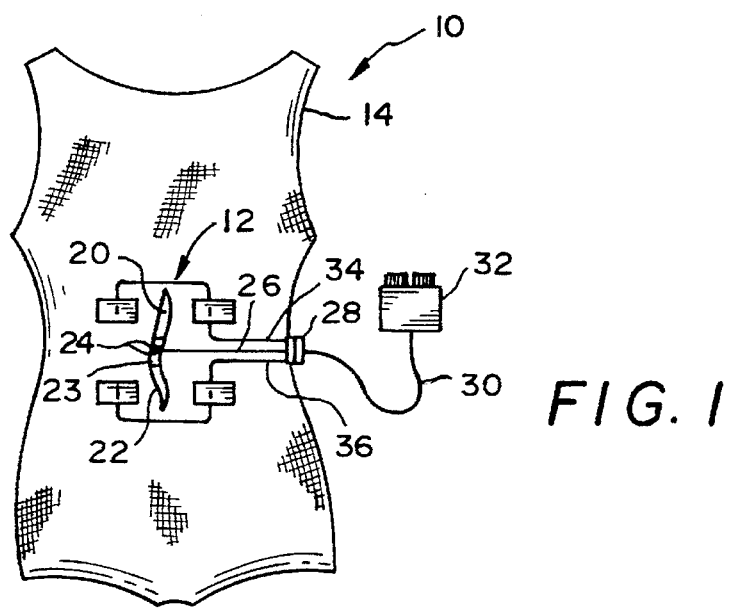

SYSTEM FOR MAINTAINING A DESIRED SPINAL CURVATURE OF A USER SUFFERING FROM IMPROPER ALIGNMENT OF THE VERTEBRAE OF THE SPINE

BACKGROUND OF THE INVENTION

1. Field of the Invention

The present invention relates generally to low back pain management systems, and more particularly, to the use of electric stimulation to alleviate suffering of a person having chronic lower back pain.

2. Description of the Related Art

A large number of individuals suffer from chronic lower back pain. Many of these individuals acquire this problem due to prolonged exposure to incorrect posture associated with occupational activities. Typical examples include: bus and truck drivers who spend long hours seated in an improper chair; secretaries and computer operators; checkout clerks in stores; factory workers; etc. The paraspinal muscles of the back, particularly the erector spinae muscles, fatigue after maintaining prolonged improper posture (Andersson, Seminars in Spine Surgery, 5,1:3–9, 1993; Cooper et al., Annals of Rheumatic Diseases, 52:413–415, 1993; also Cooper et al., Spine 18,5:610–616, 1993). The chronic fatigue of the paraspinal muscles reduces their activity level (Cassisi et al., Spine, 18,2:245–251, 1993) and causes them to be smaller and weaker (Parkkola et al., Spine, 18,7:830–836, 1993 and Hides et al., Spine, 19,2:165–172, 1994). The degeneration of the spinal muscles increases the intramuscular pressure (Styf, Spine, 12,7:675–679, 1987) and thereby reduces the circulation of blood to the neighboring structures such as muscles, vertebrae and discs (Konno et al., Spine, 19,19:2186–2189, 1994). The changes of paraspinal muscle function and blood supply causes changes in the alignment of the spine. There are discrete changes of the lower spine from Lordosis to Kyphosis (Konno et al., Spine, 19,19:2186–2189, 1994) and muscle activity which is different from their original activity during movement (Grabiner et al., Spine, 17,10:1219–1223, 1992; Sihvonen et at., Spine, 18,5:575–581, 1993). The misalignment of the spine, reduced blood circulation, and degeneration of the anatomical structures produces the low back pain which afflicts these individuals who are engaged in occupational activities which overtax the spinal muscles (Andersson, Seminars in Spine Surgery, 5,1:3–9, 1993).

Exercise and physical activity are well-known therapeutic measures for combating lower back pain, especially in the early stages of development. (Lahad et al., JAMA, 272,16: 1286–1291, 1994; Hansen et at., Spine, 18,1:98–107, 1993; Risch et al., Spine, 18,2:232–238, 1993; Frost et al., British Med Journal, 310:151–154, 1995). Unfortunately, most individuals, especially overworked drivers, factory and office personnel, fail to subscribe to daily exercise due to time or motivational constraints.

It is well established in the literature that electrical stimulation of muscles with an external stimulator can reverse the atrophy of unused muscles and fully convert them from weak, fast-to-fatigue, anaerobic muscles to strong, fatigue-resistant, aerobic muscles. (Liebet, Develop Med and Child Neurology, 28:662–670, 1986) has documented, in a review, that such reversal of muscle atrophy was demonstrated anatomically, histologically, biochemically, mechanically and electrophysiologically.

A unique, ongoing exercise of the paraspinal muscles during occupational activities without requiring the voluntary exertion of lower back pain sufferers can prevent the problem by providing continuous activation of the muscles and preserving the alignment of the spinal vertebrae.

Drs. Solomonow and D'Ambrosia have used electrical muscle stimulation for over 15 years to reverse the atrophy of lower extremity muscles in paraplegic patients, and to elicit artificial control of these muscles to induce locomotion and rehabilitation of several daily functions which were lost by the patients due to the paralysis secondary to spinal cord injury (Solomonow et al., Am J Physical Medicine, 62,2:71–82, 1983; also Solomonow et al., Am J Physical Medicine, 62,3:117–122, 1983; also Solomonow et al., Orthopedics, 12,10:1309–1315, 1989; Solomonow, In book: Neural Prostheses, R. Stein et al. (editors), Oxford Press, Chap. 10:202–232 1992; Hirokawa et al., Arch Phy Meal Rehabil, 71:687–694, 1990).

OBJECTS AND SUMMARY OF THE INVENTION

It is therefore a principal object of the present invention to provide a system which effectively provides activation of the erector spine muscles so as to preserve alignment of the spinal vertebrae.

The present invention is a system for maintaining a desired spinal curvature of a user suffering from improper alignment of the vertebrae of the spine. In it's broad aspects, it comprises a sensor feedback system and electrodes. The sensor feedback system measures spinal curvature, determines whether selected conditions have been met warranting the application of electrical stimulation and provides information regarding the determination to an electronic stimulator. The electrodes are spaceably mounted on selected portions of the user's back. They are in electrical communication with the electronic stimulator for causing contraction of the back muscles at selected levels, thus providing alignment of the spinal vertebrae.

The sensor feedback system includes a sensor assembly which comprises an upper elongated rigid segment, a lower elongated rigid segment and a sensor. The upper elongated rigid segment is positionable adjacent the user's upper spine. The lower elongated rigid segment is positionable adjacent the posterior pelvic region. The sensor is mounted on a flexible middle segment between the upper segment and the lower segment. The sensor is so positioned as to measure lordosis.

Other objects, advantages, and novel features will become apparent from the following detailed description of the invention when considered in conjunction with the accompanying drawings.

BRIEF DESCRIPTION OF THE DRAWINGS

FIG. 1 is a schematic illustration of the system of the present invention.

FIG. 2 is a perspective view of a user suffering from lower back pain, wearing the system of the present invention.

The same parts or elements throughout the drawings are designated by the same reference characters.

DETAILED DESCRIPTION OF THE PREFERRED EMBODIMENTS

Figure 3:
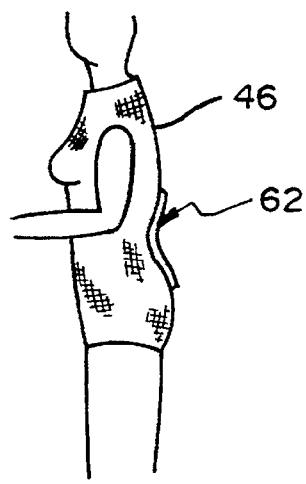
FIG. 3 is a side perspective view of a user wearing the system of the present invention, illustrating the curvature of the spine.

Referring now to the drawings and the characters of reference marked thereon, FIG. 1 illustrates a preferred embodiment of the present invention, designated generally as 10. The present system 10 includes a sensor feedback system, designated generally 12, for measuring spinal curvature. The sensor feedback system 12 includes an elastic sleeve assembly 14 which is sized to securely fit over the user's back and pelvis. The elastic sleeve is preferably formed of SPANDEX™ or similar material. It includes elongated pockets 16, 18. Elongated pockets 16, 18 contain a sensor assembly including an upper elongated rigid segment 20 and lower elongated rigid segment 22, respectively. Upper segment 20 is positionable adjacent the user's upper spine. The lower segment 22 is positionable adjacent the posterior pelvic region. A sensor 24 is operably mounted on a middle segment 23 between the upper segment 20 and lower segment 22. Sensor 24 comprises a position sensor for measuring lordosis. An example of a position sensor includes a strain gauge assembly.

An electrical conduit 26 attaches to a connector 28 on the elastic sleeve 14. The connector 28 may comprise one half of a male/female plug. This connector is attached, via cable 30, to an electrical stimulator 32. Additional electrical connections or conduits 34, 36 are also connected to connector 28. The other ends are connected to upper and lower pairs of electrodes 38, 40.

Electrodes 38, 40 may be of the type comprising carbon impregnated rubber or gel covered foils which are generally used with commercial muscle stimulation devices. They preferably have surface areas of approximately 30–45 cm², each, adjusted according to the patient's size.

The elastic sleeve 14 preferably includes pairs of rectangular window cut-outs 50 at the desirable locations of the electrodes, an upper pair 38 being positioned over an upper portion of the user's erector spinae muscles and a lower pair being positioned over a lower portion of the user's erector spinae muscles. Straps 52 are each stitched on one end thereof, to the elastic sleeve 14. The other end of each strap 52 contains a strip of adhesive material 56, commonly marketed under the trademark VELCRO™. The straps may cover each rectangular window 50. Each electrode 40 is mounted on the interior of a respective strap 52. Complementary VELCRO™ strips 54 secured to the elastic sleeve 14 provide secure attachment of each strap 52 to the sleeve 14. Each strip 52 can be flipped over its associated rectangular window 50 and fastened to VELCRO™ strips 54, allowing the electrode 40, to cover it while in direct contact with the skin's surface.

When the sensor 24 determines that selected conditions have been met, i.e. a selected degree of improper alignment of the spinal vertebrae, the voltage signal from the sensor 24 is perceived by a calibration circuit controlling a switch which is normally "off." Voltage signals which indicate smaller angles trigger the switch to the "on" condition and will activate the stimulator. Current pulses from the stimulator are conducted to the electrodes via the conduits and are passed to the muscles, causing them to contract mildly and provide forces to the vertebrae, thus providing the desired alignment.

The calibration circuit allows the patient to fine-tune the exact angle at which he desires the stimulator to be triggered into the "on" condition, thereby allowing any possible anatomical variation from person to person to be implemented.

Furthermore, the stimulator 32 preferably has two adjustment knobs to control stimulation pulse intensity and pulse frequency, respectively. This allows different patients with different degrees of misalignment levels to adjust the amount of force applied. Generally patients with severe misalignments choose higher pulse intensities and frequencies that will elicit larger forces.

Referring now to FIG. 2 and 3, the system 10 is shown applied to the body of the user 46 suffering from lower back pain. The electric stimulator 32 may be mounted on a belt 48.

A preferred stimulator 32 generally generates rectangular, charge balanced current pulses in the intensity range of 0–200 mA. The pulse frequency ranges from 20 to 2,000 Hz. Both pulse intensity and frequency are adjustable to allow the patient to calibrate the most comfortable range according to the severity of the misalignment and the level of contraction needed to prevent or correct the misalignment. In general, patients with severe misalignment may prefer higher intensities and frequencies of stimulation as compared to patients with milder misalignment.

Figures 4, 5:
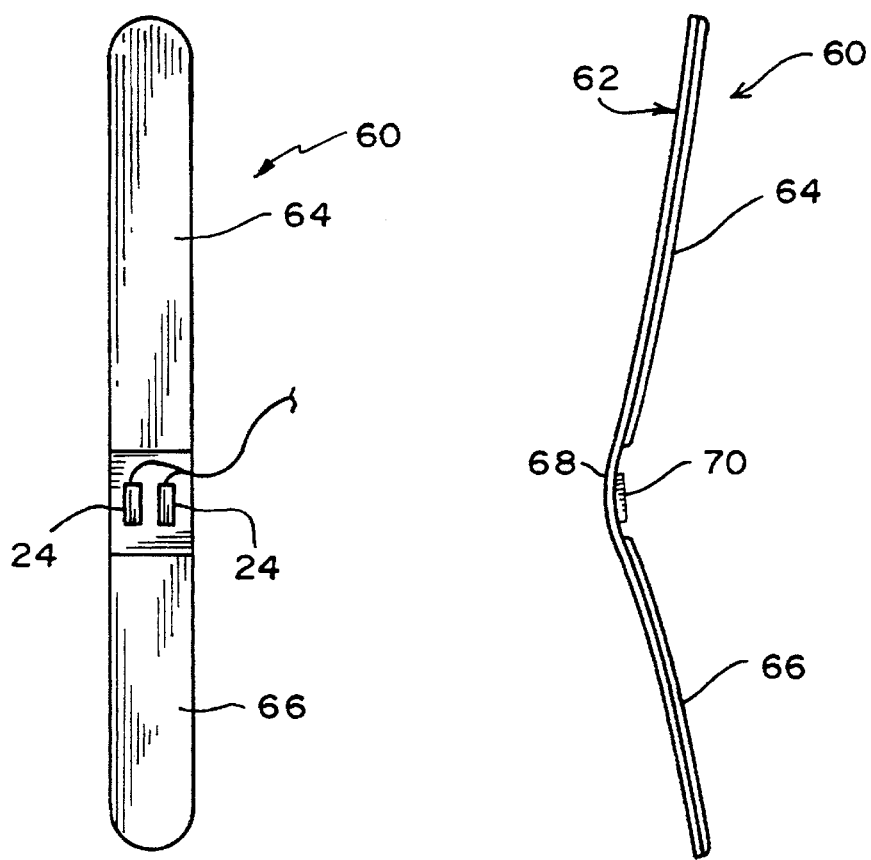
FIG. 4 is a front plan view of a sensor assembly having upper and lower segments and a sensor mounted therebetween in accordance with the principles of the present invention.
FIG. 5 is a side view of the FIG. 4 embodiment.

Referring now to FIGS. 4 and 5, a preferred embodiment of a sensor assembly, designated generally as 60, is illustrated. The sensor assembly 60 comprises an elongated plastic member 62 of sufficient length to extend from the user's upper spine to over the posterior pelvic region. The plastic member 62 is shaped, as emphasized in FIG. 3, to match the shape of the upper spine and posterior pelvic region. Plastic strips 64, 66 are mounted at upper and lower segments of the elongated plastic member 62. The use of this double layering at the upper and lower segments increases the stiffness of these (upper and lower) segments, causing most of the bending to occur in the middle segment 68. This is desired because the middle segment 68 mounts the strain gauge assembly 70. The strain gauge assembly 70 comprises a strain-gauge bridge mounted with cement on the middle segment 68. The middle segment 68 matches the natural spinal curvature of the lower back (i.e. lordosis).

The elongated member 62 is preferably, but not exclusively, formed of plastic material of about 1.5–2 mm thick and about 1 cm wide. The length will depend on the patient's size. Taller individuals require longer elastic sleeves as well as longer rigid members.

Figure 6:
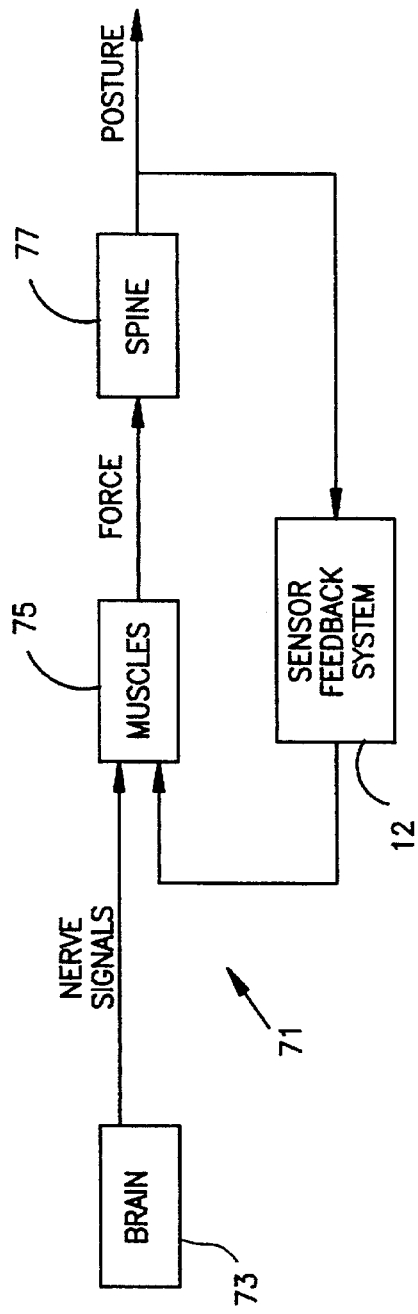
FIG. 6 is a schematic block diagram of the overall patient/sensor feedback system.

Referring now to FIG. 6, implementation of a sensor feedback system 12, of the present invention is illustrated. The sensor system 12 is interfaced with the patient's physiology as a feedback system that will assist and correct any undesirable spine posture which the patient is not capable of correcting or controlling voluntarily. The overall patient/sensor feedback system is designated 71 in FIG. 6. Voluntary control of the spine curvature is initiated by the brain structures 73, which generate electrical pulses transmitted via the spinal cord and then via peripheral nerves to the paraspinal muscles 75. The paraspinal muscles will respond to the nerve signals by contracting at appropriate levels and generating the forces necessary to create the correct alignment of the spine 77.

Figure 7:
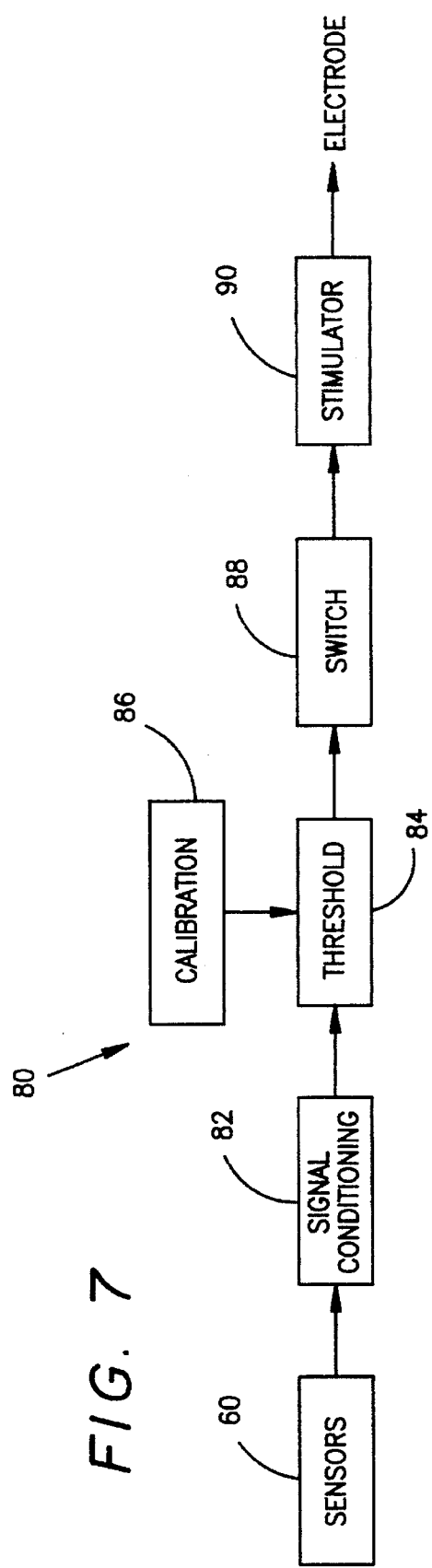
FIG. 7 is a schematic block diagram of a sensor feedback system in accordance with the principles of the present invention.

When the patient neglects to generate the appropriate nerve signals, and the spine thus assumes an incorrect and undesirable posture, the sensor feedback system 12, detects the undesirable posture and consequently activate the muscles in order to correct the posture as described below and shown in FIG. 7.

While a variety of sensors could be used to detect the deflection of the central portion of the plastic bars, strain gages are shown used, by way of example. Referring now to FIG. 7, an example of a sensor feedback system is illustrated, designated generally as 80. The strain gages from the two plastic bars are mounted in the signal conditioning section 82 in a Wheatstone configuration to linearize their output electrical signal with respect to the deflection angle of the two bars. The activation power for the strain gages is supplied from the signal conditioning section 82 as well as the amplification of the Wheatstone Bridge's current/voltage output by an operational amplifier. The changes in the current/voltage output of the Wheatstone Bridge is analyzed by a threshold circuit 84 comprising an electronic comparator. The exact voltage level, corresponding to the desirable lordosis angle at which the action of the stimulator is required, can, for example, be manually set by a calibration set-up 86 including a potentiometer with an external knob, which is adjustable by the prescribing physician or the patient himself. The function of the calibration 86 and threshold circuit 84 is to remain silent as long as the patient maintains a correct posture, and to generate a voltage when the spine curvature departs from the desirable normal angle. The voltage generated when the spine curvature becomes undesirable triggers a switch 88 that, in turn, activates the stimulator 90 and delivers pulses of sufficient magnitude to the electrodes, thereby stimulating and contracting the paraspinal muscles and causing the spine to return to the normal curvature. As the patient maintains the desirable, correct posture/curvature of the spine, the threshold circuit 84 will not generate a voltage output, and the stimulator 90 will not be active.

Several variations to this control strategy are apparent and could be implemented, all of which revolve around the concept described above.

One such variation is the addition of a timer between the switch and stimulator networks. Upon the appearance of the voltage from the switch indicating incorrect spinal posture, the timer will maintain, say, five minutes of continuous cycles stimulation (10 seconds on and five seconds off), regardless of the spinal posture. This can assist a group of patients with relatively weak muscles in strengthening these muscles in the early stages of rehabilitation.

Another practical variation is the addition of an externally and manually controlled timer that will provide 10 seconds of stimulation and five seconds rest, cycling over 10 minutes at a time when desired by the patient or when prescribed by a physician. Such a mode will provide an exercise program to the patient, strengthening his muscles and thereby allowing him better voluntary control of his spinal curvature.

An individual will benefit from wearing the present system during occupational activities requiring prolonged exposure to the same posture. Upon detection of undesirable posture of the spine, the stimulator will be activated and apply electrical pulses to the muscles. The muscles will contract and correct the deficiency in the posture by preventing misalignment. The sensor will then detect the corrected posture and de-activate the stimulator.

In addition to the modes discussed above, the system can operate in various other different modes in order to accommodate the needs of various individuals suffering from lower back pain due to postural difficulties, examples provided below:

Mode 1: As the sensor detects an abnormal lordosis angle of the spine, it activates the stimulator which, in turn, will stimulate the paraspinal muscles and correct the angle. As the angle is corrected, the sensor signal will decrease below threshold and deactivate the stimulator until such time as the lordosis angle becomes abnormal again. This mode is "on demand" mode, insuring that the spinal posture is kept in the normal range at all times.

Mode 2: Upon detection of an abnormal lordosis angle, the sensor will generate a signal which will turn on the stimulator and will keep it on for one full minute during which the sensor signal will be ignored. After the minute has elapsed, the stimulator will turn off. If the sensor detects an abnormal lordosis angle again, the process will be repeated. This mode allows for one-minute exercise which will strengthen the paraspinal muscles and allow them to gradually become effective in performing their functions.

Mode 3: As an abnormal lordosis angle is detected, the sensor will initiate a signal to the stimulator which will turn it on and provide a brief 1–2 seconds of stimulation. The stimulation will contract the muscles and will remind the wearer to continue to maintain his spine in the correct position using his voluntary action. This is a "reminder" mode, bringing the spine to the correct angle and allowing the patient to keep it there on his own (without stimulator assistance).

Mode 4: Another example of an "exercise" mode. The wearer will put the stimulator in the exercise mode which will trigger 5 minutes of cycled stimulation 2 seconds "on" and two seconds "off." This will provide strengthening of the spinal muscles during work time and allow the muscles to reverse their atrophy and resume their normal function of maintaining the correct lordosis angle.

Obviously, many modifications and variations of the present invention are possible in light of the above teachings. It is, therefore, to be understood that within the scope of the appended claims, the invention may be practiced otherwise than as specifically described.

What is claimed and desired to be secured by Letters Patent of the United States is:

1. A system for use with an electronic stimulator for maintaining a desired spinal curvature of a user suffering from improper alignment of the vertebrae of the spine, comprising:

a) a sensor feedback system for measuring spinal curvature to obtain a spinal curvature measurement, determining, using the spinal curvature measurement whether selected conditions have been met warranting the application of electrical stimulation and providing information regarding said determination to an electronic stimulator including connecting means for electrically connecting the sensor feedback system to said electronic stimulator; and b) electrodes electrically connected to said connecting means spaceably mountable on selected portions of the user's back adapted to be in electrical communication with said electronic stimulator for causing contraction of the back muscles at selected levels, thus providing alignment of the spinal vertebrae.

2. The system of claim 1, wherein said sensor feedback system, comprises:

a sensor assembly, comprising:
   a) an upper elongated rigid segment positionable adjacent the user's upper spine;
   b) a lower elongated rigid segment positionable adjacent the posterior pelvic region; and c) a sensor mounted on a flexible middle segment connecting said upper segment and said lower segment and connected to said connecting means, said sensor being so positioned as to measure lordosis.

3. The system of claim 2, wherein:

said upper segment and said lower segment have increased stiffness over said middle segment, thereby optimizing the accuracy of said sensor.

4. The system of claim 3, wherein said sensor assembly comprises:

an elongated plastic member of sufficient length to extend from the user's upper spine to over the posterior pelvic region; and plastic strips mounted at upper and lower parts of said elongated plastic member thereby forming said upper segment and said lower segments having said increased stiffness.

5. The system of claim 4, wherein said position sensor comprises a strain gauge.

6. The system of claim 2, wherein said sensor feedback system further comprises an elastic sleeve assembly sized to securely fit over the user's back and pelvis, said elastic sleeve assembly mounting said sensor assembly.

7. The system of claim 1, wherein said sensor feedback system comprises a position sensor for measuring lordosis.

8. The system of claim 1, wherein said spaceably mounted electrodes comprise two pairs of electrodes, an upper pair being mountable over an upper portion of the user's erector spinae muscles and a lower pair being mountable over a lower portion of the user's erector spinae muscles.

9. The system of claim 8, wherein a first electrode of said upper pair is mountable on the user's right erector spinae muscles and a second electrode of said upper pair is mountable on the user's left erector spinae muscles, and wherein a first electrode of said lower pair is mountable on the user's right erector spinae muscles and a second electrode of said lower pair is mountable on the user's left erector spinae muscles, thereby providing symmetrical stimulation.

10. A system for maintaining a desired spinal curvature of a user suffering from improper alignment of the vertebrae of the spine, comprising:

a) an electronic stimulator for providing an electrical stimulation signal;

b) a sensor feedback system for measuring spinal curvature to obtain a spinal curvature measurement, determining, using the spinal curvature measurement, whether selected conditions have been met warranting the application of electrical stimulation and providing information regarding said determination to said electronic stimulator; and c) electrodes spaceably mountable on selected portions of the user's back in electrical communication with said electronic stimulator for receiving said electrical signal for causing contraction of the back muscles at selected levels, thus providing alignment of the spinal vertebrae.

11. The system of claim 10, wherein said sensor feedback system, comprises:

a sensor assembly, comprising:

a) an upper elongated rigid segment positionable adjacent the user's upper spine;

b) a lower elongated rigid segment positionable adjacent the posterior pelvic region; and c) a sensor mounted on a flexible middle segment connecting between said upper segment and said lower segment, said sensor being so positioned as to measure lordosis.

12. The system of claim 11, wherein:

said upper segment and said lower segment have increased stiffness over said middle segment, thereby optimizing the accuracy of said sensor.

13. The system of claim 12, wherein said sensor assembly comprises:

an elongated plastic member of sufficient length to extend from the user's upper spine to over the posterior pelvic region; and plastic strips mounted at upper and lower parts of said elongated plastic member thereby forming said upper segment and said lower segments having said increased stiffness.

14. The system of claim 11, wherein said sensor feedback system further comprises an elastic sleeve assembly sized to securely fit over the user's back and pelvis, said elastic sleeve assembly mounting said sensor assembly.

15. The system of claim 10, wherein said sensor feedback system comprises a position sensor for measuring lordosis.

16. The system of claim 15, wherein said position sensor comprises a strain gauge.

17. The system of claim 10, wherein said spaceably mounted electrodes comprise two pairs of electrodes, an upper pair being mountable over an upper portion of the user's erector spinae muscles and a lower pair being mountable over a lower portion of the user's erector spinae muscles.

18. The system of claim 10, wherein a first electrode of said upper pair is mountable on the user's right erector spinae muscles and a second electrode of said upper pair is mountable on the user's left erector spinae muscles, and wherein a first electrode of said lower pair is mountable on the user's right erector spinae muscles and a second electrode of said lower pair is mountable on the user's left erector spinae muscles, thereby providing symmetrical stimulation.

* * * * *